US00PP15695P2

(12) United States Plant Patent
Olesen et al.

(10) Patent No.: US PP15,695 P2
(45) Date of Patent: Mar. 22, 2005

(54) HYBRID TEA ROSE PLANT 'POULEN006'

(50) Latin Name: *Rosa hybrida*
Varietal Denomination: POULen006

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/439,998

(22) Filed: May 16, 2003

(51) Int. Cl.[7] ..... A01H 5/00
(52) U.S. Cl. ..... Plt./133
(58) Field of Search ..... Plt./133

*Primary Examiner*—Bruce R. Campell
*Assistant Examiner*—S. B. McCormick-Ewoldt

(57) ABSTRACT

A new Hybrid Tea garden rose plant which has abundant, white flowers and attractive foliage. This new and distinct variety has shown to be uniform and stable in the resulting generations from asexual propagation.

2 Drawing Sheets

Classification: Botanical: *Rosa hybrida* 'POULen006'. Commercial: Hybrid Tea rose.

SUMMARY OF THE INVENTION

The present invention constitutes a new and distinct variety of garden rose plant which originated from a controlled crossing between an unnamed, non-patented seedling, and 'POULari', described and illustrated in U.S. Plant Pat. No. 9,274 issued on Sep. 5, 1994. The two parents were crossed during the summer of 1983 and the resulting seeds were planted in a controlled environment in Fredensborg, Denmark. The new variety is named 'POULen006'.

The new variety may be distinguished from its seed parent, an unnamed seedling, by the following combination of characteristics:

1. The seed parent has a petal count of 50 to 55, while that of 'POULen006' is 60 to 70.
2. The seed parent has no thorns, while 'POULen006' has many thorns.
3. The seed parent has about 170 to 180 stamens, while 'POULen006' has about 125.

The new variety may be distinguished from its pollen parent, 'POULari' by the following combination of characteristics:

1. The pollen parent has a larger bloom diameter than that of 'POULen006'.
2. The pollen parent's blooms are borne in sprays of 7 to 15 blooms, while those of 'POULen006' are borne singly.
3. 'POULen006' attains a growth height of 100 to 150 cm, while that of 'POULari' is 60 to 100 cm.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type and distinguish 'POULen006' from all other varieties of which we are aware.

As part of their rose development program, L. Pernille Olesen and Mogens N. Olesen germinated the seeds from the aforementioned hybridization during winter 1993 and conducted evaluations on the resulting seedlings in a controlled environment in Fredensborg, Denmark.

'POULen006' was selected in the spring 1994 by the inventors as a single plant from the progeny of the aforementioned hybridization.

Asexual reproduction of 'POULen006' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'POULen006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen006'. Specifically illustrated in FIG. 1:

FIG. 1.1; Open flower, stem showing branching and the attachment of leaves, buds, and peduncles;

FIG. 1.2; Partially opened flower bud;

FIG. 1.3; Flower petals, detached;

Specifically illustrated in FIG. 2:

FIG. 2.1; Sepals, receptacle, and pedicel;

FIG. 2.2; Two bare stems exhibiting thorns;

FIG. 2.3; Compound leaf;

FIG. 2.4; Juvenile leaves and shoot exhibiting anthocyanin.

DETAILED DESCRIPTION OF THE VARIETY

The following is a description of 'POULen006', as observed in its growth in a field nursery in Jackson County, Oreg. Color references are made using The Royal Horticultural Society (London, England) Colour Chart, 1995, except where common terms of color are used.

For a comparison, several physical characteristics of the rose variety 'POULen001', a rose variety from the same inventors described and illustrated in U.S. Plant patent application Ser. No. 10/264,508 dated Oct. 4, 2002 are compared to 'POULen006' in Chart 1.

CHART 1

| | 'POULen006' | 'POULen001' |
|---|---|---|
| General tonality | White Group 155C. | White group 155B at bloom perimeter; Orange-White Group 159B in center. |
| Thorn Color | Greyed-Orange Group 166B | Point of thorn is Green-Yellow Group 1C; base is Greyed-Red Group 180D. |
| Filament color | Yellow-Green 145D. | Green-Yellow Group 1D. |

Parents:

*Seed parent.*—An unnamed seedling.

*Pollen parent.*—'POULari'.

FLOWER AND FLOWER BUD

Blooming habit: Continuous.

Flower bud:

*Size.*—Upon opening, 45 mm in length from base of receptacle to end of bud.

*Bud form.*—Pointed ovoid.

*Bud color.*—As sepals unfold, Yellow-Green Group 150D, Green-White Group 157D at ¼ opening.

*Sepals.*—Upper surface is Yellow-Green Group 144A at margins, Yellow-Green Group 144B in interior. Lower surface is Yellow-Green Group 144A at margins, Yellow-Green Group 144B in interior. Variably-sized (weak to strong) foliaceous appendages on three of the five sepals. Surfaces of sepals moderately pubescent. Stipitate glands are present along the margins of the sepals. Juvenile sepals exhibit anthocyanin on underside, colored Greyed-Purple Group 183C. Shape: Sepal apex is cirrose. Base is flat at union with peduncle. Size: 25 to 35 mm long×6 to 10 mm wide.

*Receptacle.*—Surface: With fine, white hairs. Shape: Broadly funnel shaped. Size: Small. 8 mm (h)×12 mm (w). Color: Yellow-Green Group 144A.

*Peduncle.*—Surface: Smooth. Length: 45 to 50 mm average length. Color: Yellow-Green Group 144A. Strength: Strong.

*Borne.*—Singly.

*Anthocyanin.*—Color: Greyed-Purple Group 183A.

Flower bloom:

*Fragrance.*—Light, floral.

*Duration.*—The blooms have a duration on the plant of approximately 7 to 10 days.

*Size.*—Average flower diameter is 100 mm when open.

*Form.*—Shape of flower when viewed from the side: Upon opening, upper part: Convex. Upon opening, lower part: Flat. Open flower, upper part: Flattened convex. Open flower, lower part: Flattened convex.

*Petalage.*—Very double. Average range: 60 to 70 petals under normal conditions with 10 to 15 petaloids.

Color:

Upon opening, petals:

*Outermost petals.*—Outer side: White Group 155C. Inner Side: Green Yellow Group 1D.

*Innermost petals.*—Outer side: White Group 155C. Inner Side: Green Yellow Group 1D.

Upon opening, basal petal spots:

*Outermost petals.*—Outer side: Green Yellow group 1A. Inner Side: Green Yellow group 1A.

*Innermost petals.*—Outer side: Green Yellow group 1A. Inner Side: Green Yellow Group 1a.

After opening, petals:

*Outermost petals.*—Outer Side: White Group 155C. Inner Side: White Group 155C.

*Innermost petals.*—Outer Side: Whit Group 155C. Inner Side: White Group 155C.

After opening, basal petal spots:

*Outermost petals.*—Outer Side: Green-Yellow Group 1A. Inner Side: Green-Yellow Group 1A.

*Innermost petals.*—Outer Side: Green-Yellow Group 1A. Inner Side: Green-Yellow Group 1A.

General tonality: On open flower, White Group 155C. No change in the general tonality at the end of the 10th day. Afterwards, general tonality is White Group 155C.

Petals:

*Petal reflex.*—Somewhat reflexed to strongly reflexed.

*Petal edge.*—Uniform and typically reflexed along margin.

*Shape.*—Apex is round, base is round.

*Size.*—50 mm (l)×45 mm (w).

*Petaloids.*—Quantity: 10 to 15. Size: 20 to 30 mm long and 20 mm wide. Color: Yellow Group 11C on both upper and lower surfaces.

*Thickness.*—Average.

*Arrangement.*—Formal.

Reproductive organs:

*Pistils.*—Length: 13 mm long. Quantity: 80 to 90.

*Pollen.*—Quantity: None observed.

*Anthers.*—Size: 3 mm long. Color: Yellow Group 11B in interior; Yellow-Orange Group 22A at margins. Quantity: 125.

*Filaments.*—Color: Yellow-Green Group 145D. Length: 15 mm.

*Stigmas.*—Superior in location to anthers. Color: Yellow-Green Group 145D.

*Styles.*—Color: Yellow-Green Group 145D, with intonations of Red Group 39A.

*Hips.*—None observed.

PLANT

Plant growth: Vigorous, upright to bushy. When grown as a budded field grown plant on *Rosa multiflora* understock, the average height of the plant is 100 to 150 cm and the average width is 100 cm. Root development takes place in 20 to 25 days.

Stems:

*Color.*—Young wood: Yellow-Green Group 144A. Older wood: Yellow-Green Group 146B.

*Thorns.*—Incidence: 17 per 10 cm of stem. Size: 9 mm. Color: Greyed-Orange Group 166B. Shape: Deeply concave.

*Surface.*—Young wood: Smooth. Older wood: Smooth.

*Stem diameter.*—11 cm on average.

Plant foliage: Normal number of leaflets on normal leaves in middle of the stem: 5 leaflets.

*Compound leaf size.*—121 mm (l)×80 mm (w).

*Quantity.*—Average.

*Color.*—Mature Foliage: Upper Leaf Surface: Green Group 137A. Lower Leaf Surface: Green Group 143B. Juvenile foliage: Upper Leaf Surface: Green Group 137A. Lower Leaf Surface: Green Group 143B. Anthocyanin intonation: Location: New growth of top leaves, rachis, petiole and stipule. Color: Greyed-Purple Group 183A.

Plant leaves and leaflets:

*Stipules.*—Size: 10 to 15 mm length mm. Color: Yellow-Green Group 144B. Stipitate glands along the leaf margin. Anthocyanin: Greyed-Purple Group 183A.

*Petiole.*—Length: 30 mm. Color: Yellow-Green Group 145A.

*Rachis.*—Length: 30 mm. Color: Yellow-Green Group 145A.

*Leaflet.*—Edge: Serrated. Shape: Ovate. Apex is acute. Base is rounded. Glossiness: Matte. Thickness: Thick. Arrangement: Odd pinnate. Venation: Reticulate. Size: Terminal leaflets are normally 45 mm (l)×35 mm (w).

Disease resistance: Above average, resistance to mildew, rust, black spot, and *Botrytis* under normal growing conditions in Jackson County, Oreg.

Cold hardiness: The variety 'POULen006' has been found to be cold hardy in Fredensborg, Denmark and Jackson County, Oreg.

It is claimed:

1. A new and distinct variety of rose plant of the Hybrid Tea rose class, substantially as herein illustrated and described as a distinct and novel rose variety due to its abundant white flowers, disease resistance, and extended period of bloom.

* * * * *

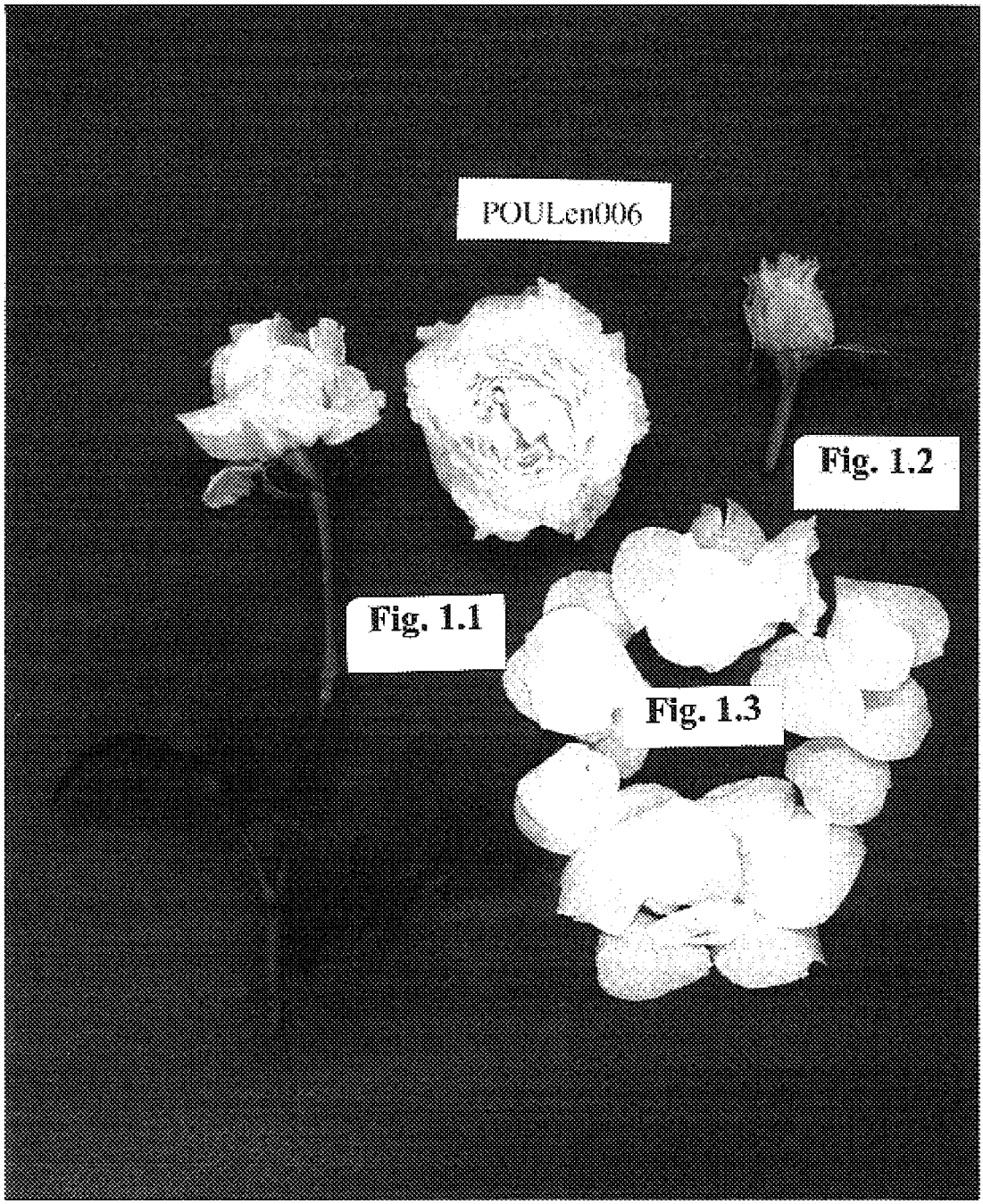
POULen006
Fig. 1.2
Fig. 1.1
Fig. 1.3

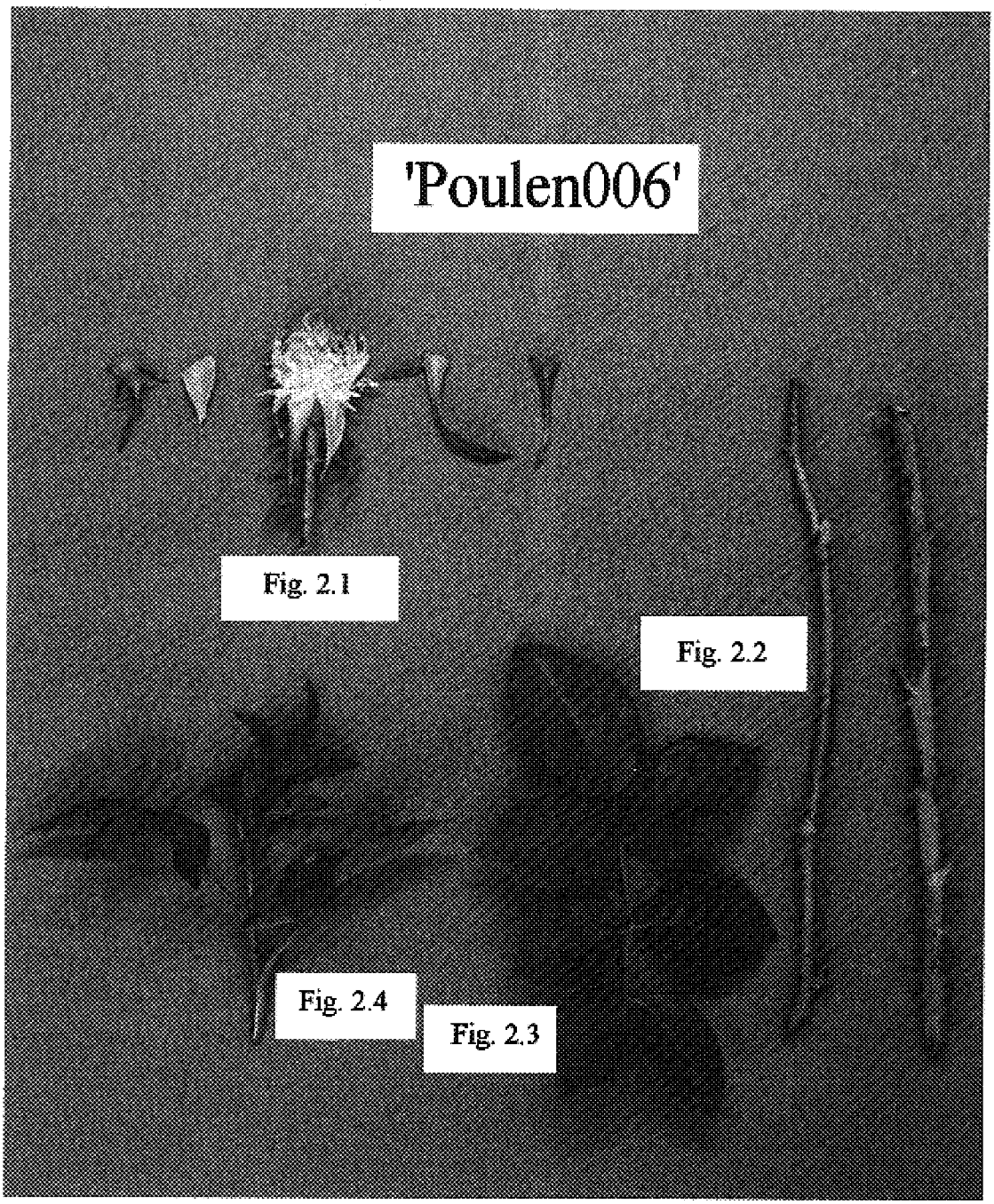
'Poulen006'
Fig. 2.1
Fig. 2.2
Fig. 2.4
Fig. 2.3